(12) United States Patent
Chamberlain et al.

(10) Patent No.: US 6,372,910 B1
(45) Date of Patent: Apr. 16, 2002

(54) PROCESS FOR THE MANUFACTURE OF 1,8-NAPHTHALIMIDE

(75) Inventors: Terrence R. Chamberlain, Montgomery; Donald T. DeRussy, Mason, both of OH (US)

(73) Assignee: Sun Chemical Corporation, Fort Lee, NJ (US)

( * ) Notice: Subject to any disclaimer, the term of this patent is extended or adjusted under 35 U.S.C. 154(b) by 0 days.

(21) Appl. No.: 09/514,609

(22) Filed: Feb. 28, 2000

(51) Int. Cl.$^7$ ............................................. C07D 221/06
(52) U.S. Cl. ........................................................ 546/98
(58) Field of Search ............................................ 546/98

(56) References Cited

U.S. PATENT DOCUMENTS

| | | | |
|---|---|---|---|
| 3,812,130 A | * 5/1974 | Landler et al. | 546/98 |
| 4,782,064 A | 11/1988 | Wright, Jr. et al. | 514/296 |
| 4,892,950 A | 1/1990 | Schutze et al. | 546/98 |

FOREIGN PATENT DOCUMENTS

| | | | | |
|---|---|---|---|---|
| DE | 2137242 A | * | 2/1973 | 546/98 |
| GB | 1346876 A | * | 2/1974 | 546/98 |
| IL | 38852 | | 11/1972 | |
| RU | 491631 | | 2/1976 | C07D/27/18 |

OTHER PUBLICATIONS

Ergalieva, A. Kh et al, Izv. Akad. Nauk KAZ. SSR, Ser. Khim. (3) 35–9 (1979) [Chemical Abstract provided].
Shalabaev, Sh B. et al, Izv. Akad. Nauk KAZ. SSR, Ser. Khim. 27 (4): 44–8, (1977) [Chemical Abstract provided].
Sembaev, D. Kh. et al, Izv. Akad. Nauk KAZ. SSR, Ser. Khim., 26 (6): 42–8 (1976) [Chemical Abstract provided].
Plakidin, V.L. et al., Zh. Org. Kihm 18(9): 1997–98 (1982) [Chemical Abstratct provided].

* cited by examiner

Primary Examiner—Alan L. Rotman
(74) Attorney, Agent, or Firm—Sidney Persley

(57) ABSTRACT

A process for preparing 1,8-naphthalimide by reacting 1,8-naphthalic anhydride with ammonia in an aqueous solution under atmospheric pressure at 60 to 100° C.

5 Claims, No Drawings

PROCESS FOR THE MANUFACTURE OF 1,8-NAPHTHALIMIDE

FIELD OF THE INVENTION

This invention relates to a process for the synthesis of 1,8-naphthalimide under atmospheric pressure at a temperature below 100° C.

BACKGROUND OF THE INVENTION 1,8-Naphthalimide is a well known intermediate for pigment and dye synthesis. The reaction of 1,8-naphthalic anhydride to produce 1,8-naphthalimide using a large excess of concentrated aqueous ammonia, performed under high temperature and pressure, is well known in the prior art. Of the major drawbacks of this known reaction process is that it produces a large amount of aqueous ammonia waste water and requires a pressure vessel.

U.S. Pat. No. 3,812,130 describes reacting solid 1,8-naphthalic anhydride with gaseous ammonia to produce 1,8 naphthalimide. The product is isolated directly by evaporating off the water. Although this procedure minimizes waste water, it still requires a pressure vessel and has the disadvantage of not allowing for any water soluble impurities or unreacted starting material to be removed after the reaction. Thus, a potentially impure product is produced.

Other sources of ammonia have been used in the prior art to react with 1,8-naphthalic anhydride. For instance, Israeli Patent IL 38852 discloses the reaction of urea with 1,8-naphthalic anhydride in refluxing xylene. This process has the disadvantage of requiring an organic solvent.

U.S. Pat. No. 4,892,950 discloses reacting ammonium sulfate with 1,8-naphthalic anhydride. This process, however, requires multiple neutralization and acid acidification steps.

The Russian Publication by Plakidin, V.L. et al., Zh. Org. Khim 18(9): 1997–8 (1982), reports using formamide as the ammonia source, but the procedure also requires high temperatures and a pressure vessel and produces a yield of only about 84%.

Another approach to the synthesis of 1,8-naphthalimide, is the oxidative ammonolysis of acenaphthene using a vanadium catalyst, as described in several Russian publications (Ergalieva, A. Kh. et al. lzv. Akad. Nauk. KAZ. SSR, Ser. Khim. (3): 35–9 1979; Shalabaev, Sh. B. et al. ibib, 27(4): 44–8, (1977); Sembaev, D. Kh. et al. ibid, 26(6): 42–8 (1976); and Russian patent SU 491631). This approach has the disadvantage of requiring high temperatures of 350–360° C.

Thus, according to the prior art, the synthesis of high yield and high purity 1,8-naphthalimide in the absence of organic solvents requires temperatures exceeding 100° C. and/or high pressure. This stems from the belief that ammonia or ammonia sources are not very reactive at temperatures below 100° C. and/or under pressures lower than atmospheric pressure.

SUMMARY OF THE INVENTION

The present invention relates to a high yield process for making a high purity 1,8-naphthalimide in the absence of an organic solvent, at a temperature below 100° C., and under a pressure atmospheric pressure while producing a minimal amount of waste water.

Other objects and advantages of the present invention will become apparent from the following description and appended claims.

DETAILED DESCRIPTION OF THE INVENTION

The process of the invention provides for an economical means to produce 1,8-naphthalimide under mild conditions in quantitative yield and high purity. It involves reacting 1,8-naphthalic anhydride with ammonia in an aqueous solution under atmospheric pressure at a temperature of about 60 to 100° C., preferably about 60 to 80° C. and more preferably about 70° C.

The amount of molar equivalents of the ammonia in the reaction is critical in achieving a good yield and a minimum amount of ammonia waste that has to be subsequently treated. A molar equivalent of ammonia of less than 1 would leave unreacted 1,8-naphthalic anhydride while a molar equivalent of more than 3.5 would yield excess unwanted ammonia waste. Therefore, the molar equivalent of ammonia employed is preferably about 1.0 to about 3.5 and more preferably about 1.2 to about 2.0.

The advantages of this process are as follows: (1) it does not require a pressure vessel; (2) runs at much lower temperatures (below 100° C.) than previously reported; (3) produces a minimal amount of waste water; and (4) does not require an organic solvent.

Monitoring the infra red spectrum of the reaction mixture with an Applied systems ReactlR 1000, it was demonstrated that the imide forms in the aqueous solution, even though water is a by-product of this step. Thus, the product can be isolated as a wet filtercake and converted directly to perylenetetracarboxylic diimide pigments through a potassium hydroxide fusion reaction without prior drying. Preferably, the yield of the process of the invention is at least 85%, more preferably at least 90% and most preferably at least 95%. This invention will next be illustrated in terms of specific examples. In these examples, as well as in the other parts of the present application, all amounts and proportions are expressed in equivalents or by weight unless otherwise indicated.

EXAMPLE 1

1,8-naphthalic anhydride (50.00 g or 0.252 mol, 1.0 eq), 32.8 mil of 29% aqueous ammonia (29.52 g, or 8.56 g dry, 0.504 mol, 2.0 eq) and water (115 g) were mixed to form a yellow slurry. The yellow slurry was then heated with stirring to 70° C. and held at that temperature for 90 minutes for a total heating time of about 2 hours. After the heating period, the mixture was cooled to room temperature and filtered. The product was then washed with 500 to 600 ml of water until the pH of the wash water was neutral (pH 7). The product was then dried in a vacuum oven at 60° C. resulting in 47.61 g of a gray solid (1,8-naphthalimide, 96% yield) having a melting point of about 301–303° C.

EXAMPLE 2

1,8-naphthalic anhydride (50.00 g, 0.252 mol, 1.0 eq), 32.8 ml of 29% aqueous ammonia (29.52% g, or 8.56 g dry, 0.504 mol, 2.0 eq) and water (115 g) were mixed to form a yellow slurry. The yellow slurry was heated with stirring to 70° C. then held at that temperature for 90 minutes for a total heating time of about 2 hours. After the heating period, the mixture was cooled to room temperature and filtered. The product was then washed with 500 to 600 ml of water until the pH of the wash water was neutral (pH 7). The product (i.e. 1,8-naphthalimide) was isolated as a wet filtercake (59.67 g, dry content=82.28%, representing 49.10 g of dry 1,8-naphthalimide, 99% yield), which was suitable for converting to 3, 4, 9, 10-perylenetetracarboxylic diimide. The purity of 1,8-naphthalimide was above 99% as determined by Gas Chromatography with a melting point of about 301–303° C.

EXAMPLE 3

1,8-naphthalic anhydride (50.00 g, 0.252 mol, 1.0 eq), 28.7 ml of 29% aqueous ammonia (25.86 g, or 7.50 g dry, 0.411 mol, 1.75 eq) and water (115 g) were mixed to form a yellow slurry. The yellow slurry was heated with stirring to 70° C., then held at that temperature for 90 minutes for a total heating time of about 2 hours. After the heating period, the mixture was cooled to room temperature and filtered. The product was then washed with 500 to 600 ml of water until the pH of the wash water was neutral (pH 7). The product was then dried in a vacuum oven at 60° C. resulting in 47.02 g of a gray solid (1,8-naphthalimide, 95% yield) having a melting point of about 300–303° C.

EXAMPLE 4

In a 500 ml reaction vessel fitted with an overhead stirrer, a temperature controller and a reflux condenser, 1,8-naphthalic anhydride (50.00 g, 0.252 mol, 1.0 eq), 24.6 ml of 29% aqueous ammonia (22.17 g, or 6.43 g dry, 0.378 mol, 1.5 eq) and water (115 g) were mixed to form a yellow slurry. The yellow slurry was heated with stirring to 70° C., then held at that temperature for 90 minutes for a total heating time of about 2 hours. After the heating period, the mixture was cooled to room temperature and filtered. The product was then washed with 500 to 600 ml of water until the pH of the wash water was neutral (pH 7). The product was then dried in a vacuum oven at 60° C. resulting in 46.21 g of a gray solid (1,8-naphthalimide, 93% yield) having a melting point of about 300–302° C.

EXAMPLE 5

In a 500 ml reaction vessel fitted with an overhead stirrer, a temperature controller and a reflux condenser, 1,8-naphthalic anhydride (50.00 g, 0.252 mol, 1.0 eq), 19.6 ml of 29% aqueous ammonia (17.69 g, or 5.13 g dry, 0.302 mol, 1.2 eq) and water (115 g) were mixed to form a yellow slurry. The yellow slurry was heated with stirring to 70?C. then held at that temperature for 90 minutes for a total heating time of about 2 hours. After the heating period, the mixture was cooled to room temperature and filtered. The product was than washed with 500 to 600 ml of water until the pH of the wash water was neutral. The product was then dried in a vacuum oven at 60° C. resulting in 43.31 g of a gray solid (1,8-naphthalimide, 87% yield) having a melting point of about 290–292° C.

EXAMPLE 6

1,8-naphthalic anhydride (50.00 g, 0.252 mol. 1.0 eq), 28.7 ml of 29% aqueous ammonia (25.86 g, or 7.50 g dry, 0.441 mol, 1.75 eq) and water (115 g) were mixed to form a yellow slurry. The yellow slurry was heated with stirring to 50° C., then held at that temperature for 90 minutes for a total heating time of about 2 hours. After the heating period, the mixture was cooled to room temperature and filtered. The product was than washed with 500 to 600 ml of water until the pH of the wash water was neutral (pH 7). The product was then dried in a vacuum oven at 60° C. resulting in 22.16 g of a gray solid (44% yield having a melting point of about 282–290° C. In addition, another 7.79 g (1,8-naphthalimide, 16% yield) of a gray solid was also isolated from the filtrates having a melting point of about 304–305° C.

EXAMPLE 7

In a 500 ml reaction vessel fitted with an overhead stirrer, a temperature controller and a reflux condenser, 1,8-naphthalic anhydride (50.00 g, 0.252 mol, 1.0 eq), 24.6 ml of 29% aqueous ammonia (22.17 g, or 6.43 g dry, 0.378 mol, 1.5 eq) and water (115 g) were mixed to form a yellow slurry. The yellow slurry was heated with stirring to 85° C., then held at that temperature for 90 minutes for a total heating time of about 2 hours. After the heating period, the mixture was cooled to room temperature and filtered. The product was then washed with 500 to 600 ml of water until the pH of the wash water was neutral (pH 7). The product was then dried in a vacuum oven at 60° C. resulting in 46.21 g of a gray solid (1,8-naphthalimide, 93% yield) having a melting point of about 300–302° C.

The present invention has been described in detail, including the preferred embodiments thereof. However, it will be apparent to those of skill in the art, upon consideration of the present disclosure, that the invention is capable of numerous modifications, substitutions, rearrangements of parts and/or improvements without departing from the spirit and scope of the invention.

What is claimed is:

1. A process for preparing 1,8-naphthalimide comprising reacting 1,8-naphthalic anhydride with about 1.0 to about 3.5 molar equivalents of ammonia in an aqueous solution under atmospheric pressure and at a temperature of about 60 to about 100° C.

2. The process of claim 1, wherein the molar equivalents of ammonia are about 1.2 to about 2.0.

3. The process of claim 1, wherein the temperature is about 60 to 80° C.

4. The process of claim 3, wherein the temperature is about 70° C.

5. The process of claim 1 resulting in a yield of 1,8-naphthalimide of at least 85%.

* * * * *

UNITED STATES PATENT AND TRADEMARK OFFICE
CERTIFICATE OF CORRECTION

PATENT NO. : 6,372,910 B1　　　　　　　　　　　　　　　　　　　　　　　Page 1 of 1
DATED : April 16, 2002
INVENTOR(S) : Chamberlain et al.

It is certified that error appears in the above-identified patent and that said Letters Patent is hereby corrected as shown below:

Column 1,
Lines 56-57, the text reading "and/or under pressures lower than atmospheric pressure" should read -- and at atmospheric pressure --.
Lines 62-63, the text reading "and under a pressure atmospheric pressure" should read -- and at atomspheric pressure --.

Signed and Sealed this

Eighth Day of October, 2002

Attest:

Attesting Officer

JAMES E. ROGAN
*Director of the United States Patent and Trademark Office*